US008343160B2

(12) United States Patent
Techiera et al.

(10) Patent No.: US 8,343,160 B2
(45) Date of Patent: Jan. 1, 2013

(54) PIVOTING IMPLANT HOLDER

(75) Inventors: Richard C. Techiera, New Bedford, MA (US); Sean P. Selover, Westport, MA (US)

(73) Assignee: DePuy Spine, Inc., Raynham, MA (US)

( * ) Notice: Subject to any disclaimer, the term of this patent is extended or adjusted under 35 U.S.C. 154(b) by 585 days.

(21) Appl. No.: 12/637,900

(22) Filed: Dec. 15, 2009

(65) Prior Publication Data
US 2010/0094359 A1   Apr. 15, 2010

Related U.S. Application Data

(63) Continuation of application No. 10/737,538, filed on Dec. 16, 2003, now Pat. No. 7,648,507, and a continuation of application No. 10/737,166, filed on Dec. 16, 2003, now Pat. No. 7,648,506.

(51) Int. Cl.
*A61B 17/70* (2006.01)

(52) U.S. Cl. ..................... 606/86 A; 606/914

(58) Field of Classification Search .............. 606/86 A, 606/86 B, 99, 914–916
See application file for complete search history.

(56) References Cited

U.S. PATENT DOCUMENTS

| | | | |
|---|---|---|---|
| 714,364 A | 11/1902 | Cogan | |
| 791,548 A | 6/1905 | Fischer | |
| 1,016,607 A | 2/1912 | Booman | |
| 1,047,003 A | 12/1912 | Diehl | |
| 1,412,284 A | 4/1922 | Hellman | |
| 1,519,938 A | 12/1924 | Smith | |
| 1,855,477 A | 4/1932 | Emery | |
| 2,028,635 A | 1/1936 | Wappler | |
| 2,498,465 A | 2/1950 | Thomas | |
| 3,835,735 A | 9/1974 | Carr | |
| 4,134,157 A | 1/1979 | Laure | |
| 4,201,213 A | 5/1980 | Townsend | |
| 4,418,692 A | 12/1983 | Guay | |
| 4,461,194 A | 7/1984 | Moore | |
| 4,572,179 A | 2/1986 | Teitelbaum et al. | |
| 4,590,936 A | 5/1986 | Straub et al. | |
| 4,655,216 A | 4/1987 | Tischer | |
| 4,763,669 A | 8/1988 | Jaeger | |
| 4,880,015 A | 11/1989 | Nierman | |
| 5,061,270 A | 10/1991 | Aboczky | |
| 5,083,621 A | 1/1992 | Sheridan | |
| 5,170,925 A | 12/1992 | Madden et al. | |

(Continued)

FOREIGN PATENT DOCUMENTS
WO    0217823 A1    3/2002

*Primary Examiner* — Sameh Boles
(74) *Attorney, Agent, or Firm* — Nutter McClennen & Fish LLP

(57) ABSTRACT

A medical inserter tool is provided for introducing medical implants into a surgical site, preferably using minimally invasive techniques. The inserter tool can have a variety of configurations, but in general, the inserter tool should be effective to engage and manipulate the implant into two or more positions. In an exemplary embodiment, the tool includes an elongate shaft having proximal and distal ends and defining a longitudinal axis extending therebetween, and a pivoting element that is coupled to the distal end of the shaft and that is adapted to engage a spinal implant. In use, the pivoting element is movable between first and second positions to allow an implant to be introduced through a percutaneous access device in a lengthwise orientation, and to be manipulated subcutaneously to be positioned in a desired orientation.

20 Claims, 13 Drawing Sheets

U.S. PATENT DOCUMENTS

| | | | |
|---|---|---|---|
| 5,209,747 | A | 5/1993 | Knoepfler |
| 5,352,223 | A | 10/1994 | McBrayer et al. |
| 5,374,277 | A | 12/1994 | Hassler |
| 5,393,036 | A | 2/1995 | Sheridan |
| 5,549,637 | A | 8/1996 | Crainich |
| 5,618,294 | A | 4/1997 | Aust et al. |
| 5,634,584 | A | 6/1997 | Okorocha et al. |
| 5,688,276 | A | 11/1997 | Shaffer |
| 5,782,834 | A | 7/1998 | Lucey et al. |
| 5,782,859 | A | 7/1998 | Nicholas et al. |
| 5,797,917 | A | 8/1998 | Boyd et al. |
| 5,851,207 | A | 12/1998 | Cesarone |
| 5,857,723 | A | 1/1999 | Mathieu et al. |
| 5,904,689 | A | 5/1999 | Jonjic |
| 5,906,629 | A | 5/1999 | Oren et al. |
| 6,059,790 | A | 5/2000 | Sand et al. |
| 6,066,142 | A | 5/2000 | Serbousek et al. |
| 6,102,934 | A | 8/2000 | Li |
| 6,110,179 | A | 8/2000 | Flivik et al. |
| 6,325,810 | B1 | 12/2001 | Hamilton et al. |
| 6,342,057 | B1 | 1/2002 | Brace et al. |
| 6,379,364 | B1 | 4/2002 | Brace et al. |
| 6,506,208 | B2 | 1/2003 | Hunt et al. |
| 6,575,899 | B1 | 6/2003 | Foley et al. |
| 6,712,819 | B2 | 3/2004 | Zucherman et al. |
| 7,011,665 | B2 | 3/2006 | Null et al. |
| 7,179,261 | B2 | 2/2007 | Sicvol et al. |
| 7,335,207 | B1 | 2/2008 | Smith |
| 7,341,587 | B2 | 3/2008 | Molz, IV et al. |
| 7,527,638 | B2 | 5/2009 | Anderson et al. |
| 2001/0021853 | A1 | 9/2001 | Heckele et al. |
| 2002/0069538 | A1 | 6/2002 | Tanton |
| 2002/0116824 | A1 | 8/2002 | Herrmann et al. |
| 2003/0208203 | A1* | 11/2003 | Lim et al. ............... 606/61 |
| 2004/0039384 | A1* | 2/2004 | Boehm et al. ........... 606/61 |
| 2005/0090824 | A1* | 4/2005 | Shluzas et al. .......... 606/61 |

* cited by examiner

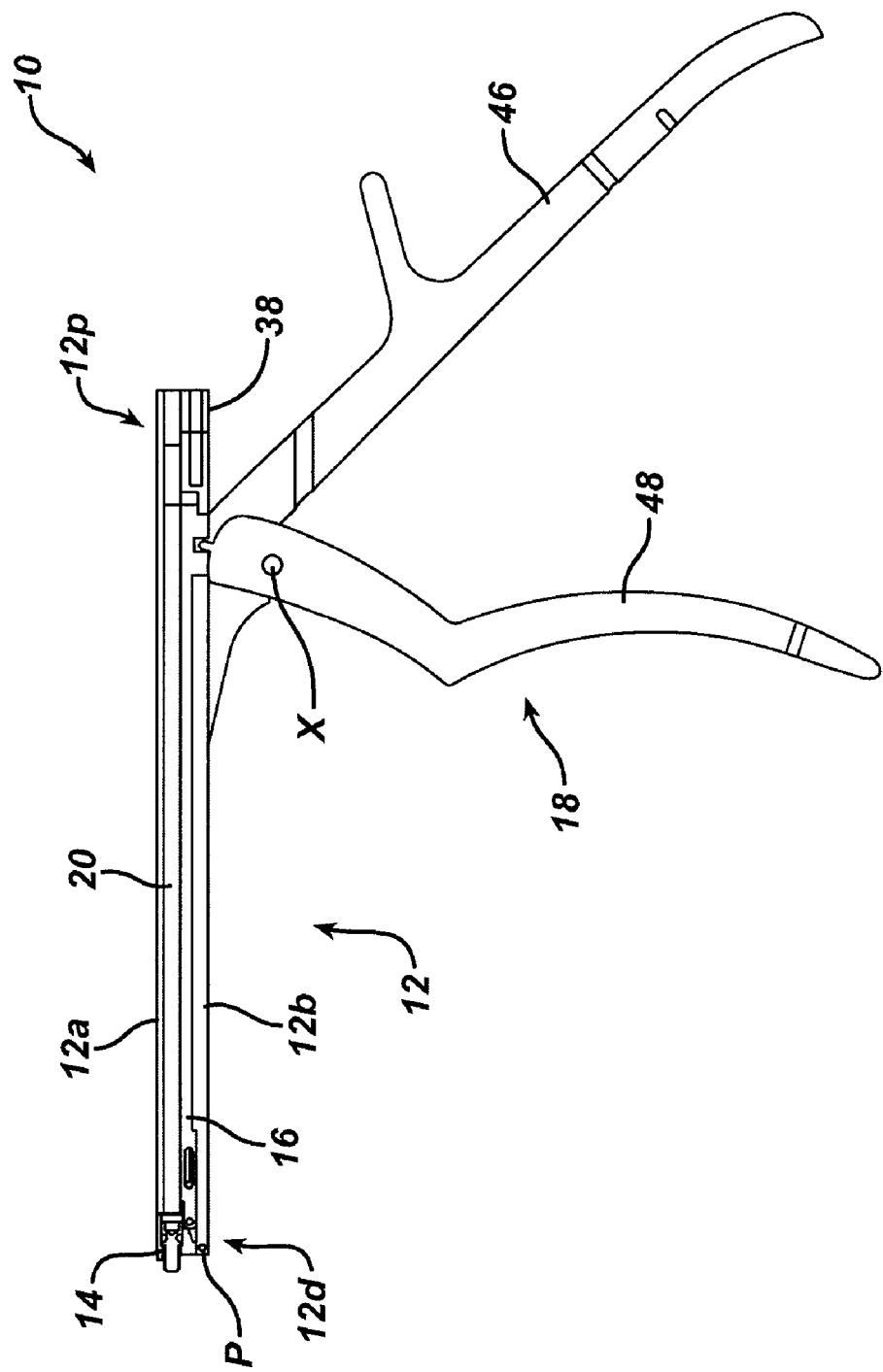

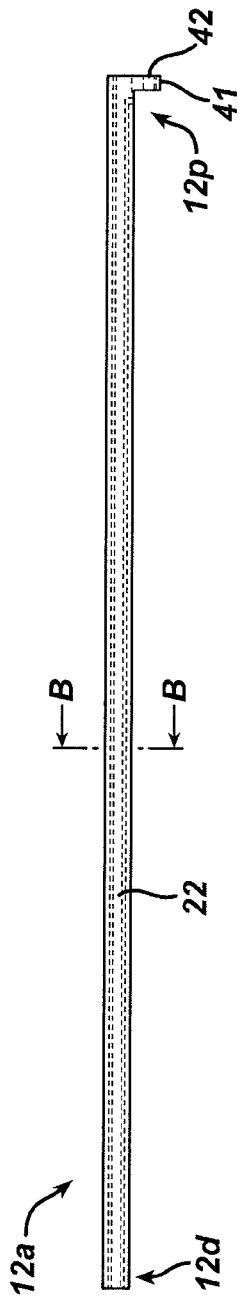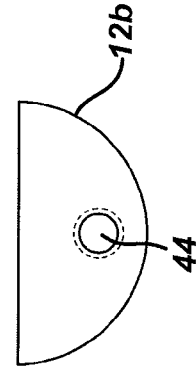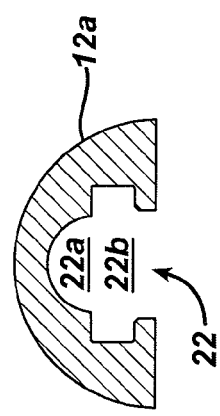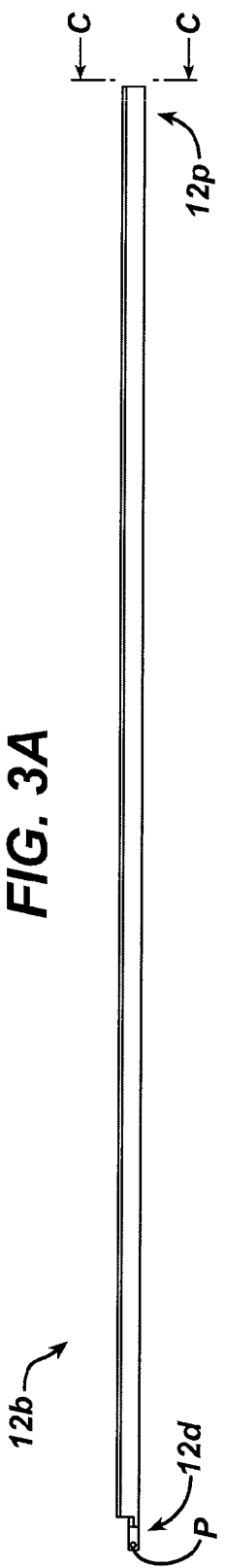

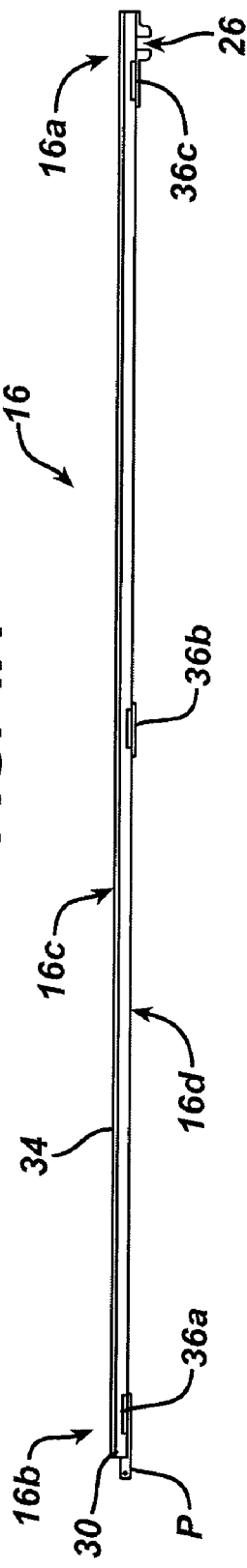
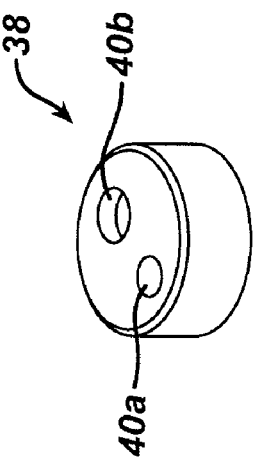
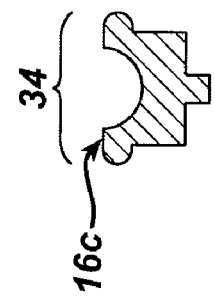

PIVOTING IMPLANT HOLDER

CROSS REFERENCE TO RELATED APPLICATIONS

This application is a continuation of U.S. application Ser. No. 10/737,538 filed on Dec. 16, 2003 and entitled "Pivoting Implant Holder", now U.S. Pat. No. 7,648,507 and U.S. application Ser. No. 10/737,166 filed on Dec. 16, 2003 and entitled "Pivoting Implant Holder", now U.S. Pat. No. 7,648,506, which are hereby incorporated by reference in their entireties.

FIELD OF THE INVENTION

This application relates to tools for use in spinal surgery, and in particular to methods and devices for introducing implants into a surgical site using minimally invasive techniques.

BACKGROUND OF THE INVENTION

Traditional surgical procedures for pathologies located deep within the body can cause significant trauma to intervening tissues. These open procedures often require a long incision, extensive muscle stripping, prolonged retraction of tissues, denervation and devascularization of tissue. Accordingly, minimally invasive surgery provides several advantages over conventional open-incision surgery because it involves creating small incisions or portals in the patient to access percutaneous bone, organs, and soft tissues. Small incisions are less traumatic to the patient and they provide for accelerated recovery and convalescence. Minimally invasive surgery can also be less time consuming and less expensive than conventional surgery.

Minimally invasive surgical approaches are particularly desirable in spinal surgery because of the need for access to locations deep within the body and the risk of damage to vital intervening tissues. Several new spinal surgery techniques have been developed that utilize percutaneous access devices, such as cannulas and trocars, to introduce surgical instruments and/or implants into a surgical site. These recent developments have yielded a significant improvement in reducing recovery time and post-operative pain because they require minimal muscle dissection and they can often be performed under local anesthesia.

The use of percutaneous access device in spinal surgery can, however, present difficulty in introducing implants and/or instruments into a surgical site since percutaneous access devices limit the surgeons ability to control movement of instruments and devices passing therethrough. Often the percutaneous access devices have an inner diameter that is smaller than the length of the implant and/or instrument being received therein. Most percutaneous access devices also only permit direct, in-line access to a surgical site, thus making it more difficult to manipulate and/or control the instrument and/or implant.

Accordingly, there remains a need for methods and devices for introducing implants into a surgical site using minimally invasive techniques.

SUMMARY OF THE INVENTION

The present invention provides a medical implant inserter tool that generally includes an elongate shaft having proximal and distal ends defining a longitudinal axis extending therebetween, and a pivoting element coupled to the distal end of the elongate shaft and adapted to releasably engage a medical implant, such as a spinal rod. The pivoting element is movable between a first position, in which the pivoting element is longitudinally aligned with the shaft, and a second position, in which the pivoting element is substantially transverse to the shaft. This allows elongate implants to be introduced through a percutaneous access device in a lengthwise fashion, and then to be rotated to its implanted orientation and positioned as desired. The tool also includes an actuator mechanism that is coupled to the proximal end of the elongate shaft and that is effective to move the pivoting element between the first and second positions.

In one embodiment, the actuator mechanism can be a trigger formed on the proximal end of the elongate shaft, and a pusher shaft slidably disposed with respect to the elongate shaft and extending between the trigger and the pivoting element such that movement of the trigger is effective to move the pusher shaft to effect pivoting movement of the pivoting element between the first and second positions. In an exemplary embodiment, the pivoting element is biased to the first position, preferably by a biasing element that is coupled to the trigger. As a result, actuation of the trigger is effective to move the pivoting element into the second position.

In another embodiment of the present invention, the pivoting element can include a threaded engagement mechanism, such as a set screw, that is adapted to releasably engage an implant. A driver shaft can be coupled to the elongate shaft and it can include a distal end that is effective to rotate the threaded engagement mechanism in the pivoting element. In an exemplary embodiment, the driver shaft is separated from the threaded engagement mechanism when the pivoting element is in the second position, and the driver shaft is coupled to and effective to rotate the threaded engagement mechanism when the pivoting element is in the first position. The threaded engagement mechanism can optionally include a socket formed in a proximal end thereof for receiving the distal end of the driver shaft. The socket of the pivoting element and the distal end of the driver tool preferably have complementary shapes.

The present invention also provides a spinal implant kit that includes a spinal rod having proximal and distal, and a spinal rod holder. The spinal rod holder preferably has an elongate shaft with a distal end that is adapted to releasably engage the proximal end of the spinal rod and to move the rod between a first position, in which the rod is substantially parallel with the longitudinal axis of the spinal rod holder, and a second position, in which the rod is substantially transverse to the longitudinal axis of the spinal rod holder. In an exemplary embodiment, a pivoting element is pivotally coupled to a distal end of the elongate shaft and it is movable between the first and second positions. A cam mechanism, such as a pin and slot arrangement, can be provided between the pivoting element and the elongate shaft to allow movement of the pivoting element between the first and second positions. In use, the pivoting element can be adapted to engage the spinal rod internally, and more preferably the rod can include a threaded bore formed on a proximal end thereof for receiving a threaded engagement mechanism that is rotatably disposed in the pivoting element.

The present invention also provides a method for percutaneously introducing a spinal rod into a surgical site. The method includes the step of introducing an elongate rod holder having a spinal rod mated to a distal end thereof into a percutaneous access device, such as a trocar, with the rod oriented in a direction that is substantially parallel to a longitudinal axis of the rod holder. The percutaneous access device preferably provides a minimally invasive pathway to the surgical site. The rod holder is then advanced through the percutaneous access device to position the rod at a surgical site, and it is used to move the rod into a position in which the rod is oriented in a direction that is substantially transverse to the longitudinal axis of the rod holder. The rod can then be released from the rod holder, and the rod holder is then removed from the percutaneous access device.

BRIEF DESCRIPTION OF THE DRAWINGS

FIG. 1B is a cross-sectional view taken along a longitudinal axis of the instrument shown in FIG. 1A;

FIG. 2A is a side, partially transparent view of an upper portion of the elongate shaft of the medical inserter tool shown in FIGS. 1A and 1B;

FIG. 2B is a cross-sectional view of the upper portion of the elongate shaft shown in FIG. 2A taken across line B-B;

FIG. 3A is a side view of a lower portion of the elongate shaft of the medical inserter tool shown in FIGS. 1A and 1B;

FIG. 3B is a cross-sectional end view of the lower portion of the elongate shaft shown in FIG. 3A taken across line C-C;

FIG. 4A is a side view of a pusher shaft of the medical inserter tool shown in FIGS. 1A and 1B;

FIG. 4B is a cross-sectional view of the pusher shaft of FIG. 4A taken across line A-A;

FIG. 5 is a side perspective view of an o-ring retaining member of the medical inserter tool shown in FIGS. 1A and 1B;

DETAILED DESCRIPTION OF THE INVENTION

The present invention provides a medical inserter tool that can be used to introduce a medical implant into a surgical site, preferably using minimally invasive techniques. The inserter tool can have a variety of configurations, but in general, the inserter tool should be effective to engage and manipulate the implant into two or more positions. In an exemplary embodiment, the tool includes an elongate shaft having proximal and distal ends and defining a longitudinal axis extending therebetween, and a pivoting element that is coupled to the distal end of the shaft and that is adapted to engage a spinal implant. In use, the pivoting element is movable between a first position, in which the pivoting element is substantially longitudinally aligned with the shaft, and a second position, in which the pivoting element is substantially transverse to the longitudinal axis of the shaft. The device also preferably includes an actuator mechanism that is effective to move the pivoting element between the first and second positions.

The medical inserter tool of the present invention is particularly advantageous in that it enables reliable and controlled movement of an implant between several orientations, and in particular it allows an implant, preferably one having an elongate configuration, to be inserted through a percutaneous access device in a lengthwise orientation, and then to be manipulated to position the implant as required for implantation, which can be at an angle with respect to a longitudinal axis of the percutaneous access device. The medical inserter tool can also advantageously be adapted to selectively engage and disengage the implant, thus allowing the tool to be easily removed from the implant once it is implanted. A person skilled in the art will appreciate that the medical inserter tool can have a variety of configurations, and it can be used to deliver a variety of implants to a surgical site, either using minimally-invasive techniques or using conventional surgical approaches.

Figure 1A:
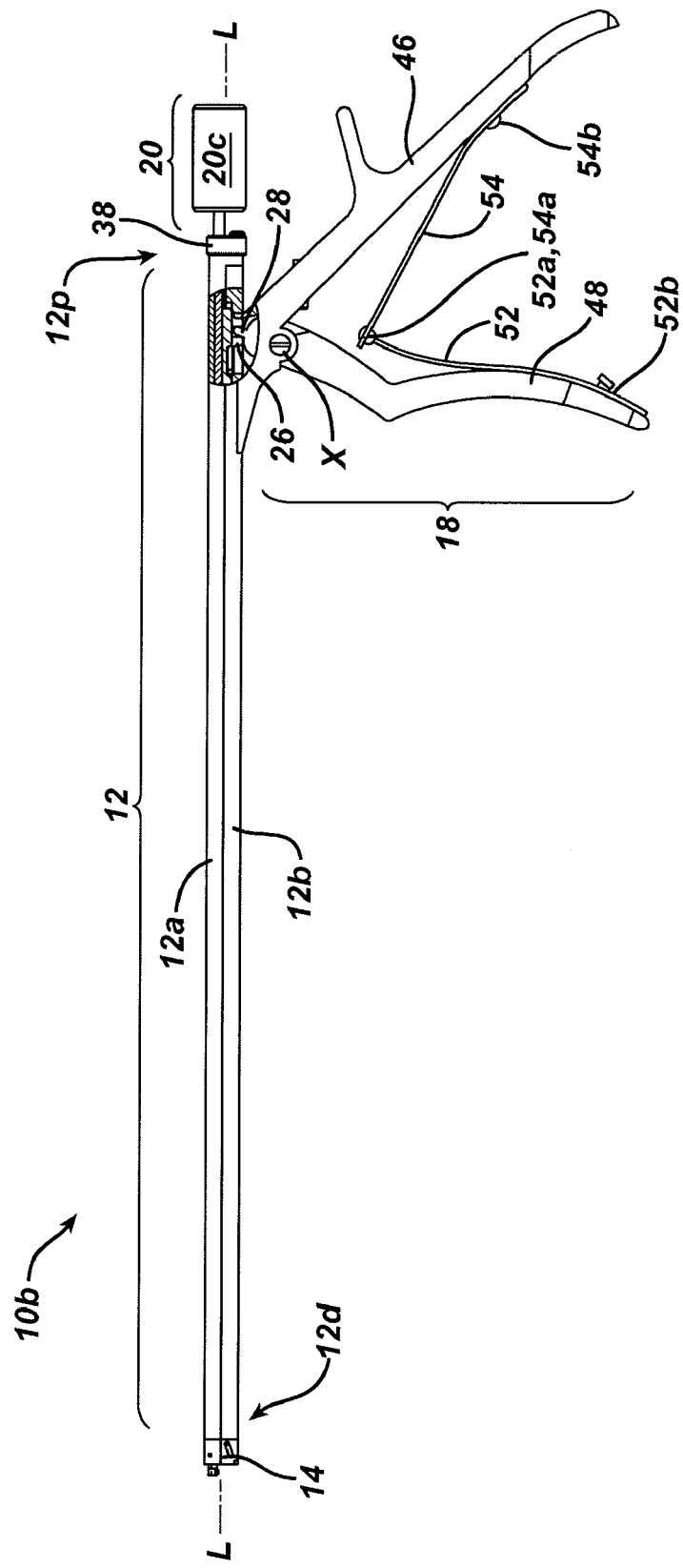
FIG. 1A is a side, partially cut-away view of a medical implant inserter tool in accordance with one embodiment of the present invention.

FIGS. 1A and 1B illustrate an exemplary embodiment of a medical inserter tool 10 in accordance with the present invention. As shown, the tool 10 generally includes an elongate shaft 12 having a pivoting element 14 that is pivotally coupled to a distal end 12d thereof and that is effective to engage an implant. The tool 10 also includes an actuator mechanism, e.g., a trigger 18, that is coupled to a proximal end 12p of the elongate shaft 12, and that is effective to move a pusher shaft 16 that is slidably disposed with respect to the elongate shaft 12, which in turn is effective to move the pivoting element 14 between a first position, in which the pivoting element 14 is longitudinally aligned with the elongate shaft 12, as shown, and a second position, in which the pivoting element 14 is substantially transverse to a longitudinal axis L of the shaft 12 (see FIG. 7B). Such movement of the pivoting element 14 allows an implant to be introduced lengthwise through a percutaneous access device, with the implant in a position that is substantially in-line with the longitudinal axis L of the tool 10, and then to be subcutaneously pivoted into a desired position, which is preferably transverse to the longitudinal axis L of the tool 10. The tool 10 also includes a driver shaft 20, only a portion of which is shown in FIG. 1A, that is effective to couple to a mating element on the pivoting element 14 to engage and/or release an implant from the pivoting element 14.

The elongate shaft 12 of the inserter tool 10 can have a variety of configurations, and it can be formed from one or more components. By way of non-limiting example, the elongate shaft 12 can optionally be formed from one or more elongate tubes having one or more lumens and/or cavities formed therein. In an exemplary embodiment, the elongate shaft 12 has a generally cylindrical shape and it includes proximal and distal ends 12p, 12d that define a longitudinal axis L. As shown in FIGS. 2A-3B, the elongate shaft 12 is formed from upper and lower portions 12a, 12b, which are illustrated separated from one another. Each portion 12a, 12b of the shaft 12 can have a generally elongate, hemi-spherical shape such that, when the portions 12a, 12b are combined, they form a generally cylindrical, elongate shaft 12. The upper and lower portions 12a, 12b also define a cavity therein when joined that is effective to slidably receive the pusher shaft 16, and to rotatably seat the driver shaft 20. A person skilled in the art will appreciate that, while not illustrated, the driver shaft and/or the pusher shaft can have any configuration, and they can be disposed anywhere in relation to the elongate shaft 12.

The upper portion 12a of the elongate shaft 12 is shown in more detail in FIGS. 2A and 2B, and it includes a cavity 22 formed therein and extending between the proximal and distal ends 12p, 12d thereof. The cavity 22, which can be in the form of a lumen, is preferably effective to receive the driver shaft 20, as well as a portion of a pusher shaft 16, each of which will be discussed in more detail below. While the shape of the cavity 22 can vary depending on the shape of the driver shaft 20 and the pusher shaft 16, the illustrated cavity 22 includes a hemi-spherical concave portion 22a, and a substantially T-shaped portion 22b. The hemi-spherical concave portion 22a seats a portion of the driver shaft 16, which has a generally cylindrical shape, and the T-shaped portion 22b is effective to receive a T-shaped member 34 that extends along the length of the top of the pusher shaft 16 to mate the upper portion 12a to the pusher shaft 16. The T-shaped member 34 and the corresponding T-shaped portion 22b are advantageous in that they allow the pusher shaft 16 to slide with respect to the upper portion 12a. A person skilled in the art will appreciate that virtually any mating technique can be used to provide a sliding connection between the pusher shaft 16 and the upper portion 12a.

The lower portion 12b of the elongate shaft 12, which is shown in FIGS. 3A and 3B, also mates to the pusher shaft 16, and it can also include a variety of mating elements formed thereon for mating to the pusher shaft 16. Again, the mating element should be effective to allow slidable movement of the pusher shaft 16 with respect to the lower portion 12b. In an exemplary embodiment, the lower portion 12b includes one or more pin members (not shown) formed thereon that are adapted to be disposed within one or more corresponding grooves 36a-c (FIG. 4A) formed on a bottom surface of the pusher shaft 16, which will be discussed below. The pins can be configured to press-fit into the grooves 36a-c on the pusher shaft 16 to prevent removal of the lower portion 12b from the pusher shaft 16, yet to allow slidable movement therebetween.

The pusher shaft 16 is shown in FIG. 4A, and it can have a variety of configurations. By way of non-limiting example, the pusher shaft 16 can have a generally cylindrical, elongate shape, or it can be in the form of a pusher bar or rod. In the illustrated embodiment, the pusher shaft 16 is in the form of a generally elongate rod and, as previously stated, the pusher shaft 16 includes a T-shaped member 34 that extends along the length of a top surface 16c thereof, and it includes one or more pin members (not shown) formed on a bottom surface 16d thereof. In addition, as shown in FIG. 4B, the pusher shaft 16 can also include a hemi-spherical concave portion 17 formed in the T-shaped member 34 that is effective to seat a portion of the driver shaft 18. The concave portion 22a on the upper portion 12a of the elongate shaft 12 and the concave portion on the pusher shaft 16 together form an elongate, cylindrical lumen that is effective to receive the driver shaft 18. The lumen, i.e., the concave portions, should be adapted to allow free rotation of the driver shaft 18.

When the upper portion 12a, pusher shaft 16, and lower portion 12b are all mated to one another, as shown in FIGS. 1A and 1B, the pusher shaft 16 is allowed to slide between and with respect to the upper and lower portions 12a, 12b. Movement between the upper and lower portions 12a, 12b, however, should be prevented. Accordingly, in an exemplary embodiment, the upper and lower portions 12a, 12b are mated to one another by an o-ring type retainer member 38. The retainer member 38 is shown in FIG. 5 and it generally includes two bores 40a, 40b extending therethrough. The first bore 40a, which is the smaller bore, is adapted to receive a threaded member, e.g., a screw, that is effective to threadably mate to a threaded bore 42 formed in a transverse member 41 (FIG. 2A) that is formed on the proximal end 12p of the upper portion 12a. The screw (not shown) also extends into a threaded bore 44 (FIG. 3B) that is formed on the distal end 12d of the lower portion 12b. Accordingly, the bore 42 in the transverse member 41 on the upper portion 12a (FIG. 2A) is adapted to align with the bore 44 formed on the distal end 12d of the lower portion 12b of the elongate shaft. The second, larger bore 40b in the retainer member 38 is effective to receive the driver shaft 18, which extends between the upper portion 12a and the pusher shaft 16, and which will be discussed in more detail below.

As previously stated, the tool 10 also includes a pivoting element 14, which is shown in FIGS. 6A-7B. The pivoting element 14 should be effective to engage an implant and to manipulate the implant into two or more positions. The range of motion of the pivoting element 14 can vary depending on the type of implant used, as well as the desired positioning of the implant. In an exemplary embodiment, however, the pivoting element 14 is movable between a first position, shown in FIG. 7A, in which the pivoting element 14 is substantially longitudinally aligned with the longitudinal axis L of the elongate shaft 12, and a second position, shown in FIG. 7B, in which the pivoting element 14 is positioned substantially transverse to the longitudinal axis L of the elongate shaft 12.

While the pivoting element 14 can mate to any portion of the elongate shaft 12 and/or the pusher shaft 16, the pivoting element 14 is preferably adapted to pivotally mate to the distal end 12d of the lower portion 12b of the elongate shaft 12 to allow the pusher shaft 16 to effect pivotal motion of the pivoting element 14 about the lower portion 12b of the elongate shaft 12. Virtually any mating technique known in the art can be used to pivotally mate the pivoting element 14 to the lower portion 12b including, for example, a pin member that is disposed through bores formed in the pivoting element 14 and the lower portion 12b. In an exemplary embodiment, the pivoting element 14 mates to the distal-most end 12d of the lower portion 12b at pivot point P, as shown.

Figure 6A:
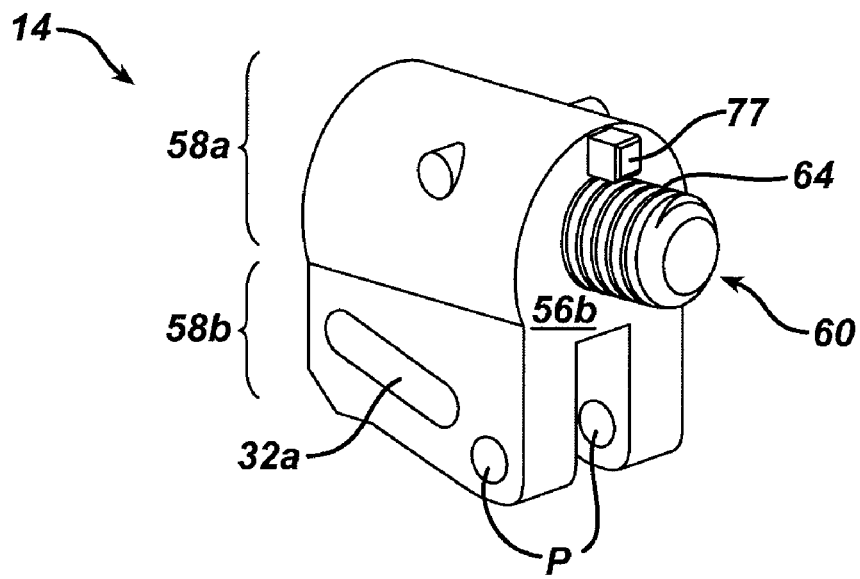
FIG. 6A is a distal, side perspective view of a pivoting element of the medical inserter tool shown in FIGS. 1A and 1B.
Figure 6B:
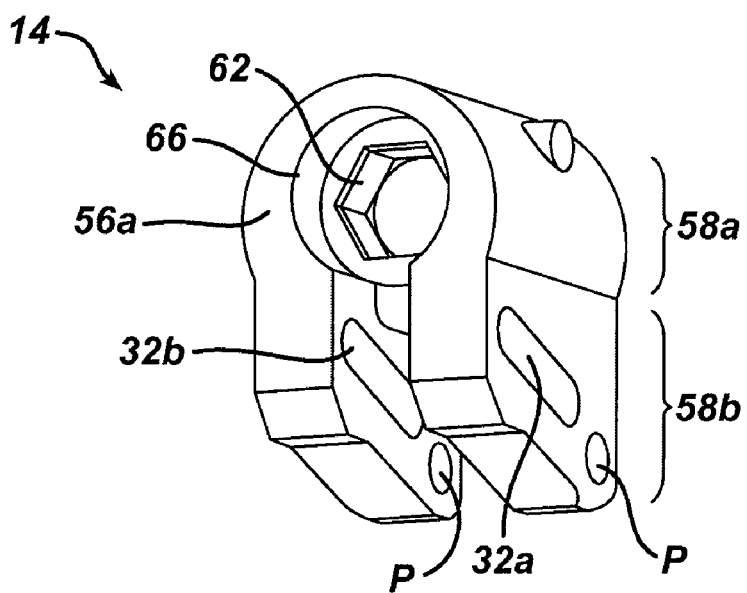
FIG. 6B is a proximal, side perspective view of a pivoting element of the medical inserter tool shown in FIGS. 1A and 1B.
Figure 7A:
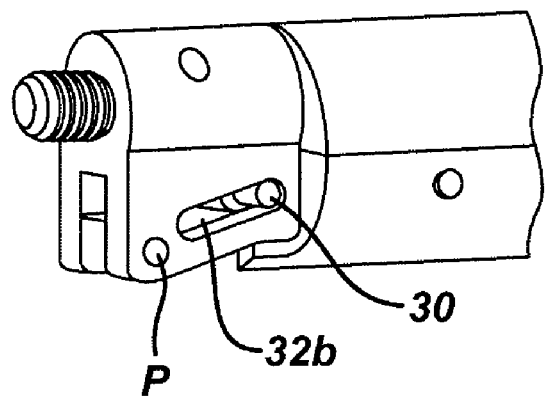
FIG. 7A is a perspective view of the distal end of the medical inserter tool shown in FIGS. 1A and 1B with the pivoting element in a first position.
Figure 7B:
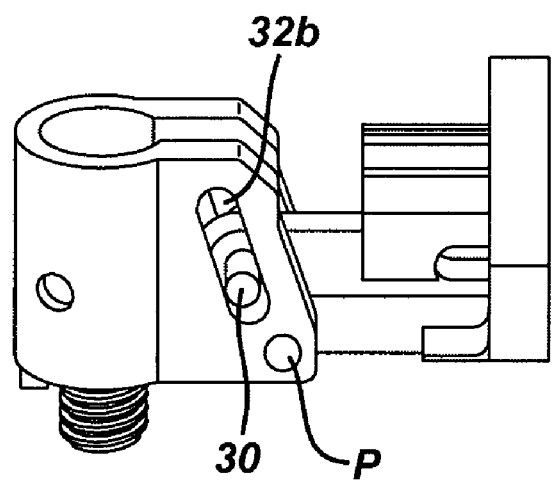
FIG. 7B is a perspective view of the distal end of the medical inserter tool shown in FIGS. 1A and 1B with the pivoting element in a second, pivoted position.

In order to move the pivoting element 14 between the first and second positions, the distal end 16b of the pusher shaft 16 can be adapted to apply a force to the pivoting element 14 to rotate it about the pivot point P, or the pusher shaft 16 can employ other techniques that are effective to move the pivoting element 14. In an exemplary embodiment, however, the distal end 16b of the pusher shaft 16 is coupled to the pivoting element 14 in a manner that results in simultaneous movement of the pivoting element 14 as the pusher shaft 16 is moved in distal and proximal directions. While a variety of techniques can be used to couple the distal end 16b of the pusher shaft 16 to the pivoting element 14, in the illustrated embodiment the pusher shaft 16 includes opposed pin members (only one pin member 30 is shown; see also FIGS. 7A and 7B) formed thereon that are adapted to extend into opposed slots 32a, 32b (FIGS. 6A-7B) that are formed in the pivoting element 14. The opposed slots 32a, 32b are positioned at an angle which results in movement of the pivoting element 14 as the pusher shaft 16 is moved. In particular, distal movement of the pusher shaft 16, by actuation of the trigger 18, causes the pins 30 to slide within the slots 32a, 32b, thus forcing the pivoting element 14 to pivot, moving from the first position, shown in FIG. 7A, to the second position, shown in FIG. 7B. Release of the trigger 18 will subsequently cause the pusher shaft 16 to move in a proximal direction, thus causing the pins 30 to slide in the opposite direction within the slots 32a, 32b, pulling the pivoting element 14 back to the first position (FIG. 7A).

Figure 8:
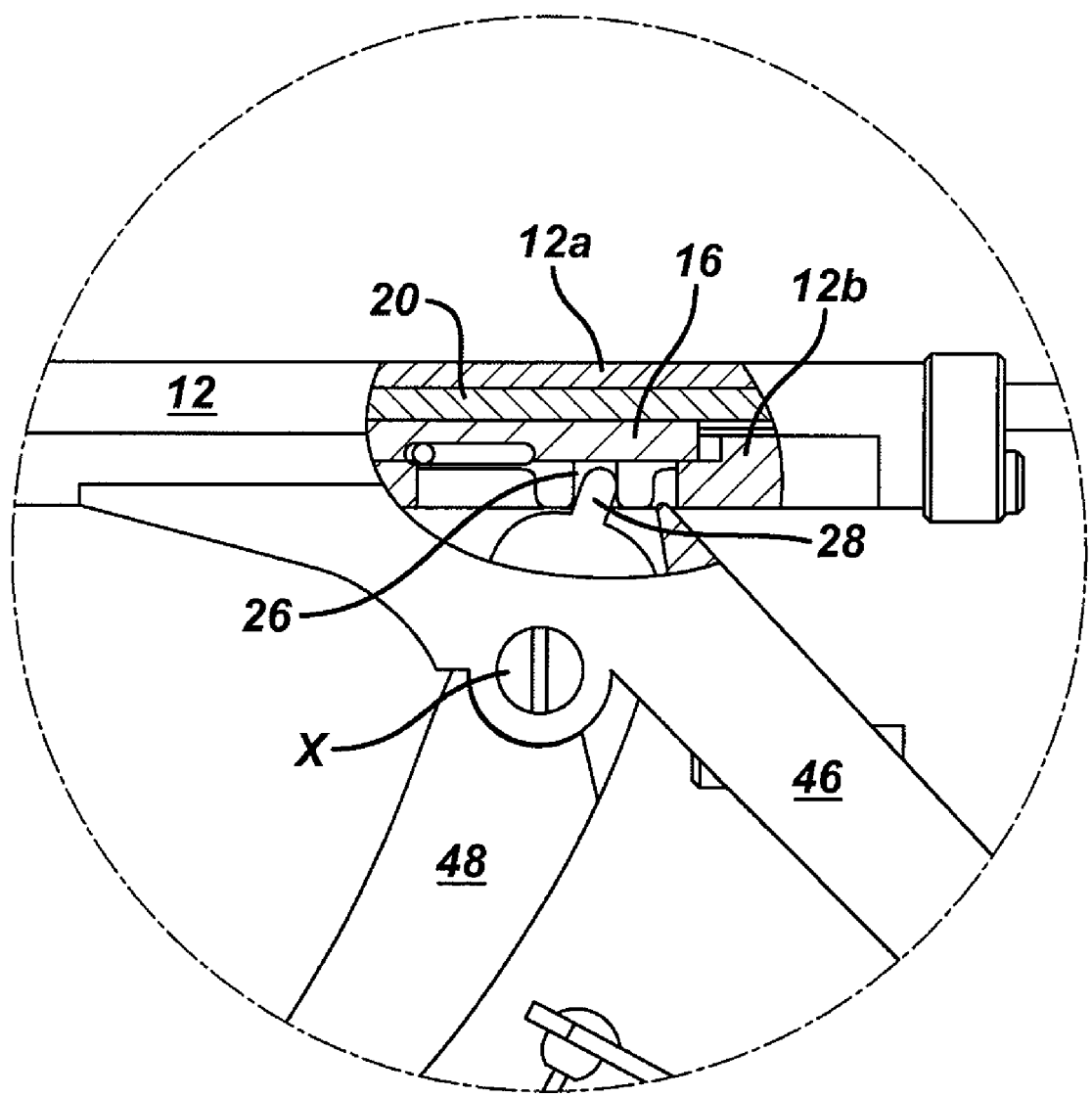
FIG. 8 is an enlarged, partially cut-away view of a portion of the medical inserter tool shown in FIGS. 1A and 1B.

An exemplary embodiment of a trigger 18 that is effective to move the pusher shaft 16 is shown in FIGS. 1A, 1B, and 8. As shown, the trigger 18 is coupled to a proximal end 12a of the tool 10 and it is effective to move the pusher shaft 16, thereby moving the pivoting element 14. The trigger 18 includes a stationary handle 46 that is fixedly attached to a proximal end 12p of the elongate shaft 12, and a pivoting handle 48 that is pivotally coupled to the stationary handle 46 at pivot point X. The end of the pivoting handle 48 that is adjacent to the pivot point X includes a protrusion or cam 28 formed thereon that is adapted to extend into the corresponding detent or cam surface 26 formed on a proximal portion of the pusher shaft 16, as shown in FIG. 8. Thus, when the pivoting handle 48 is brought toward the stationary handle 46, the cam 28 is rotated to push the pusher shaft 16 in a distal direction. Conversely, release of the pivoting handle 48 is effective to pull the pusher shaft 16 back into its original, proximal position. A person skilled in the art will appreciate that a variety of other techniques can be used to effect sliding movement of the pusher shaft 16, and/or to control pivotal movement of the pivoting member 14.

In another embodiment of the present invention, the trigger 18 can include a biasing element that is effective to bias the pivoting handle 48 such that a force effective to overcome the biasing force is necessary to move the pivoting handle 48 toward the stationary handle 46. As a result, the biasing element in turn is effective to bias the pivoting element 14 to the first position. While virtually any biasing element can be used, in an exemplary embodiment, shown in FIG. 1A, the biasing element is formed from male and female spring components 52, 54 that are positioned between the pivoting handle 48 and the stationary handle 46, as shown in FIG. 1A. Each component has a first end 52a, 54a that mates to one of the pivoting handle 48 and the stationary handle 46, and a second end 52b, 54b that couples to one another and that creates the biasing force between the handles 46, 48.

In use, referring back to FIGS. 6A-7B, the pivoting element 14 is adapted to mate to an implant, and thus the configuration, shape, and size of the pivoting element 14 can vary depending on the intended use. In the illustrated embodiment, the pivoting element 14 is configured to mate to a spinal bone plate. In general, the pivoting element 14 includes a proximal end 56a, a distal end 56b, and top and bottom portions 58a, 58b extending therebetween. As previously indicated, the distal end 56b of the bottom portion 58b of the pivoting element 14 pivotally mates to the distal end 12d of the lower portion 12b of the elongate shaft 12 at pivot point P, and the proximal end 56a of the bottom portion 58b includes the opposed elongate slots 32a, 32b that receive the pin members 30 on the pusher shaft 16 to effect pivoting movement of the pivoting element 14.

The top portion 58a of the pivoting element 14 includes a mating element that is adapted to releasably engage a spinal bone plate. While virtually any mating element can be used, in an exemplary embodiment, as shown, a set screw 60 is freely rotatably disposed within a bore 66 that extends through the top portion 58a in the proximal-distal direction. The set screw 60 includes a head having a socket 62 formed therein, and a distally-extending threaded shank 64 that is adapted to be threadably disposed within a threaded bore formed in a spinal bone plate. The socket 62 in the head of the set screw 60 has a shape that is complementary to a shape of the outer surface of a distal end 20b of the driver shaft 20, which is discussed below. As shown in FIG. 6B, the socket 62 is hexagonally-shaped. The complementary shapes allow the driver shaft 20 to rotate the set screw 60 when the driver shaft 20 is disposed therein. It also allows the driver shaft 20 to be easily separated from the pivoting element 14, thus allowing the pivoting element 14 to be moved between the first and second positions.

A person skilled in the art will appreciate that the pivoting element can have a variety of configurations, and it can be adapted such that use of a driver shaft is not necessary. By way of non-limiting example, the pivoting element could be in the form of a housing having a mandrel or hole containing spring clips and/or deflectable rings or arms.

Figure 9A:
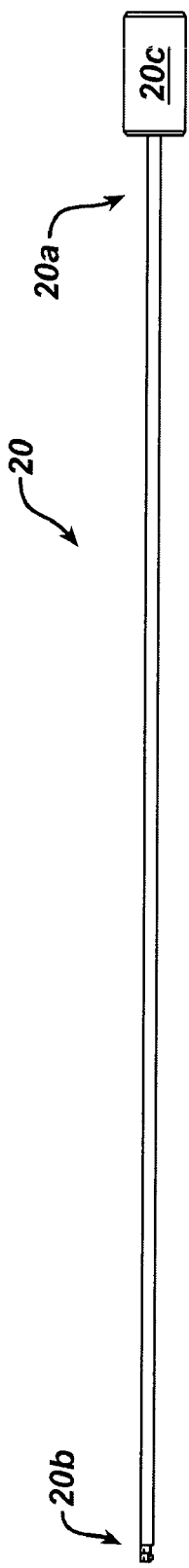
FIG. 9A is a side view of a driver shaft of the medical inserter tool shown in FIGS. 1A and 1B.
Figure 9C:
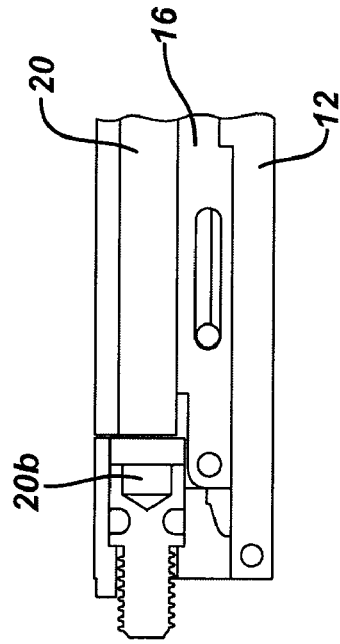
FIG. 9C is a cross-sectional, side view of a distal portion of the medical inserter tool shown in FIGS. 1A and 1B.
Figure 9B:
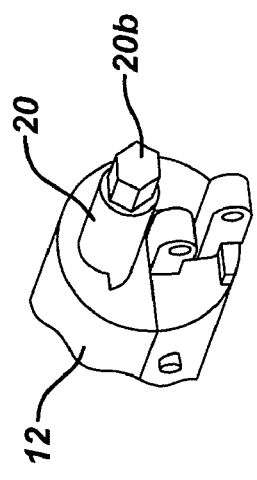
FIG. 9B is a distal, side perspective view of a distal portion of the medical inserter tool shown in FIGS. 1A and 1B.

The driver shaft 20 can have any configuration, but an exemplary embodiment of a driver shaft is shown in FIGS. 9A-9C. As shown, the driver shaft 20 has a generally elongate shape and includes a proximal end 20a with a handle or gripping knob 20c formed thereon or mated thereto, and a distal end 20b that is adapted to couple to the set screw 60 to rotate the set screw 60. While the configuration of the distal end 20b can vary depending on the configuration of the set screw 60, or other mating element on the pivoting element 14, in an exemplary embodiment the distal end 20b of the driver shaft 20 has an outer surface that complements the shape of the socket 62 in the set screw 60, such as, for example, a hexagonal shape. As previously stated, a portion of the driver shaft 18 extends through the retainer member 38, which is thus effective to maintain the position of the driver shaft 18 with respect to the elongate shaft 12 by preventing longitudinal movement, yet allowing rotational movement, of the driver shaft 18. This can be achieved using, for example, an o-ring (not shown) that is disposed within the second bore 40b, or by providing other mechanisms such as, for example, pins, spring clips, and/or deflectable rings/arms.

In use, the driver shaft 20 is disposed between the pusher shaft 16 and the upper portion 12a of the elongate shaft 12 such that the proximal end 20a of the driver shaft 20 extends through the o-ring in the second bore 40b in the retainer member 38, and the knob 20c is positioned proximally to the retainer member 38. The distal end 20b of the driver shaft 20 is configured to be disposed within the socket 62 in the set screw 60 when the pivoting element 14 is in the first position, as shown in FIG. 9C. In this position, rotation of the driver shaft 20 is effective to rotate the set screw 60 and thereby engage a spinal implant. Conversely, when the pivoting element 14 is moved into the second position, shown in FIG. 7B, the distal end 20b of the driver shaft 20 (the driver shaft 20 is hidden by the pusher bar in FIG. 7B) is separated from the pivoting element 14. As a result, an implant mated to the pivoting element 14 can only be released from the pivoting element 14 when the pivoting element 14 is coupled to the driver shaft 20, i.e., when the pivoting element 14 is in the first position.

Figure 10A:
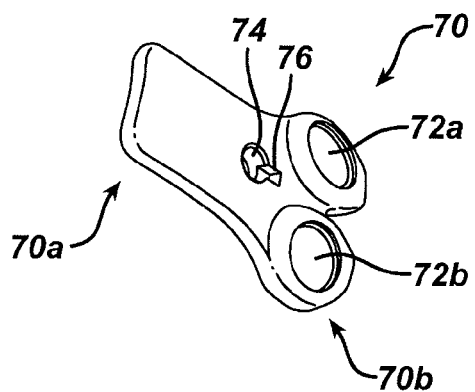
FIG. 10A is a perspective view of one embodiment of an anterior buttress plate for use with the medical inserter tool shown in FIGS. 1A and 1B.

Referring now to FIG. 10A, an exemplary embodiment of a spinal bone plate 70 for use with the tool 10 of the present invention is shown. In general, the plate 70 is an anterior buttress plate and it has a substantially planer configuration with opposed first and second ends 70*a*, 70*b*. The second end 70*b* includes first and second screw bores 72*a*, 72*b* formed therein for receiving a bone screw to attach the plate 70 to a vertebra. The plate 70 also includes a threaded bore 74 formed at a substantial mid-portion thereof for threadably receiving the set screw 60 on the pivoting element 14.

Figure 10B:
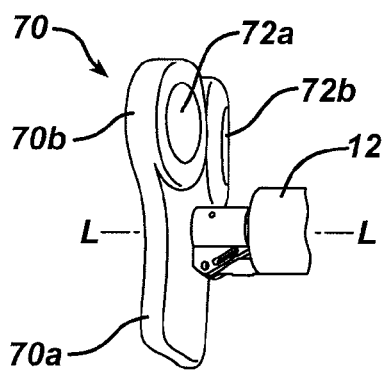
FIG. 10B is a side perspective view of the anterior buttress plate shown in FIG. 10A mated to the pivoting element of the medical inserter tool shown in FIGS. 1A and 1B.

In order to engage the plate 70 using tool 10, the distal end 12*d* of the elongate shaft 12 is positioned relative to the plate 70, as shown in FIG. 10B, such that the plate 70 extends in a direction that is substantially transverse to the longitudinal axis L of the elongate shaft 12. The knob 20*c* on the driver shaft 20 is then grasped and rotated to thread the set screw 60 into the bore 74 in the plate 70, thus mating the plate 70 to the pivoting element 14. The trigger 18 can then be actuated to move the pivoting element 14 and the plate 70 into the second position, shown in FIG. 10C, in which the plate 70 is substantially in-line with the longitudinal axis L of the elongate shaft 12. In this position, the plate 70 and the shaft 12 can be introduced through a percutaneous access device to deliver the plate 70 to an implant site. Once fully extended through the access device, the trigger 18 can be released, thus causing the pivoting element 14 to return to the first position and the plate 70 to return to the substantially transverse position. One or more bone screws can then be inserted through the screw bores 72*a*, 72*b* in the plate 70 to attach the plate 70 to bone, and the driver shaft 20 can be rotated in an opposite direction to disengage the set screw 60 from the plate 70, thus releasing the tool 10 from the plate 70.

In another embodiment of the present invention, the pivoting element 14 can include an anti-rotation mechanism formed thereon to prevent the plate 70 from rotating relative to the pivoting element 14 when they are mated to one another. While the anti-rotation mechanism can have any configuration, in the illustrated embodiment it is in the form of a protrusion 77, shown in FIG. 6A, that extends distally from the distal end of the pivoting element 14, preferably at a location that is adjacent to the set screw 60. The protrusion 77 is configured to fit within a corresponding detent 76 formed in the spinal bone plate 70, as shown in FIG. 10A. A person skilled in the art will appreciate that a variety of other techniques can be used to prevent rotation between an implant and the pivoting element 14.

FIGS. 11-14 illustrate yet another embodiment of a medical implant inserter tool 100. In this embodiment, the inserter tool 100 is specifically adapted for use with a spinal fixation rod 170. Inserter tool 100 is similar to inserter tool 10 is most aspects, thus like reference numbers are used to refer to like parts. In general, the spinal rod inserter tool 100 includes an elongate shaft 112 having proximal and distal ends 112*p*, 112*d*, and an inner lumen 112*c* extending therebetween. Unlike tool 10, the elongate shaft 112 is preferably formed from a single elongate tube having an inner lumen or cavity formed therein that seats only the pusher shaft (not shown). The configuration of the shaft 112 can, however, include any number of components and/or lumens/cavities extending therethrough or formed therein. The pusher shaft is similar to pusher shaft 16, and it includes a proximal end that is coupled to a trigger 118, and a distal end that is coupled to a pivoting element 114. The trigger 118 can function similar to trigger 18 of tool 10, and the pusher shaft can be coupled to the pivoting element 114 in the same manner that pusher shaft 16 is coupled to pivoting element 14 of tool 10.

The inserter tool 100 can also include a driver shaft (not shown) that is effective to rotate a threaded engagement mechanism, such as set screw 160, that is disposed within the pivoting element 114. The driver shaft is similar to driver shaft 20 of inserter tool 10, however, is not disposed through the elongate shaft 112 as with inserter tool 10, but rather it is removably disposed through a bore 113 that extends through a proximal end 112*p* of the shaft 112 adjacent to the trigger 118. The bore 113 is preferably offset from the longitudinal axis E of the elongate shaft 112. This is desired to allow the driver shaft to couple to the set screw 160 in the pivoting element 114 when the pivoting element 114 is in the second, pivoted position (FIG. 12), as will be discussed in more detail below.

Figure 11:
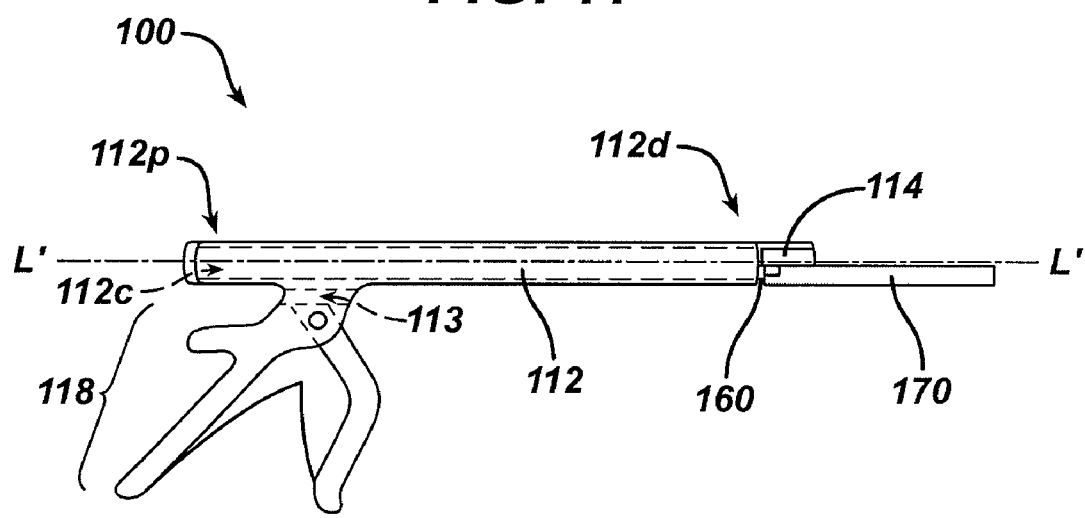
FIG. 11 is a partially-transparent side view of another embodiment of a medical inserter tool in accordance with the present invention having a spinal rod mated thereto and positioned perpendicular to a longitudinal axis of the tool.
Figure 12:
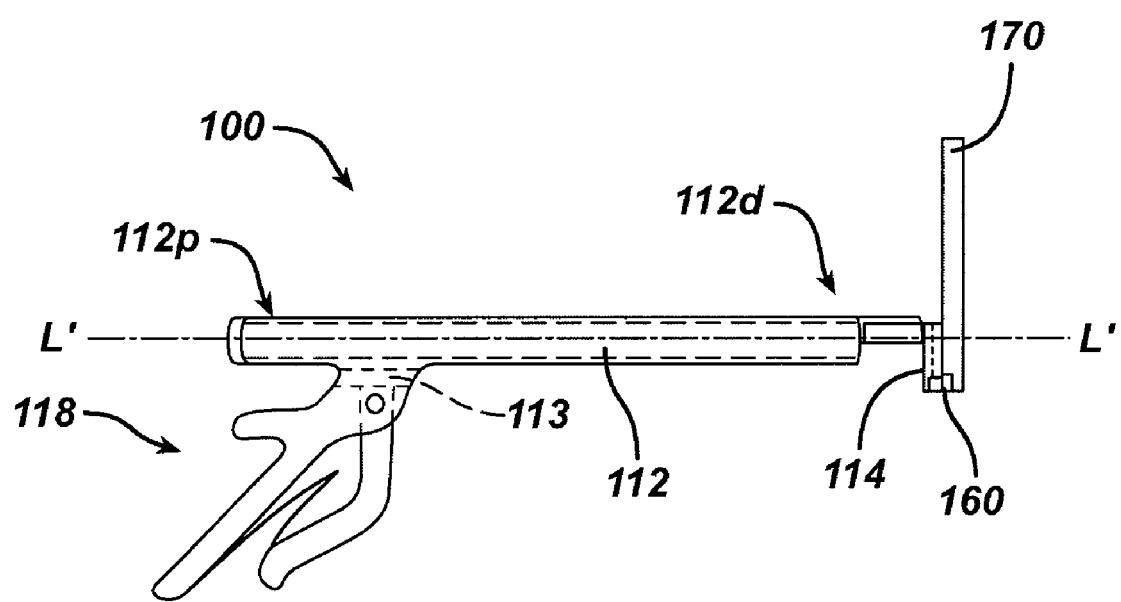
FIG. 12 is a partially-transparent side view the medical inserter tool of FIG. 11 with the spinal rod positioned transverse to the longitudinal axis of the tool.

While tool 100 is generally similar to tool 10, one significant difference is the pivoting element 114. As shown in FIGS. 11-12, the pivoting element 114 is effective to engage the spinal rod 170 such that the rod 170 is substantially in-line with the longitudinal axis L' of the elongate shaft 112 when the pivoting element 114 is in the first position, unlike inserter tool 10 which maintains the spinal bone plate 70 in a position that is substantially transverse to the longitudinal axis L of the elongate shaft 12 when the pivoting element is in the first position. Actuation of the trigger 118 is effective to rotate the pivoting element 114, thus rotating the rod 170 to be positioned substantially transverse to the longitudinal axis L'.

Figure 13A:
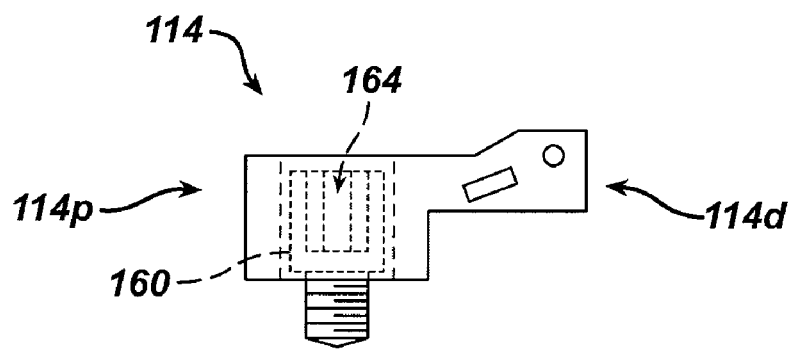
FIG. 13A is a side, partially transparent view of a pivoting element of the medical inserter tool shown in FIG. 11.
Figure 13B:
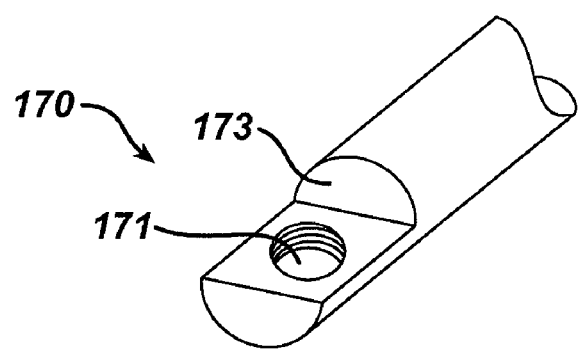
FIG. 13B is a perspective view of a portion of the spinal rod shown in FIG. 11.

FIGS. 13A-13B illustrate pivoting element 114 and spinal rod 170 in more detail. As shown, the pivoting element 114 includes a distal end 114*d* that pivotally mates to the distal-most end 112*d* of the elongate shaft 112, and a proximal end 114*p* that is adapted to mate to the spinal rod 170. In this embodiment, the set screw 160 extends through the proximal end 114*p* and it is adapted to engage a corresponding bore 171 formed in the spinal rod 170. The proximal portion 114*p* of the pivoting element 114 can also optionally be adapted to be received by a cut-out portion 173 in the spinal rod, as shown in FIG. 13B, to prevent rotation between the pivoting member 114 and the rod 170 when mated to one another.

Figure 13C:
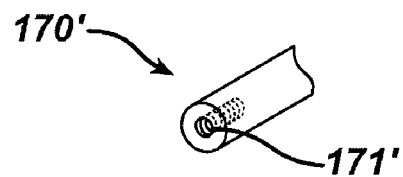
FIG. 13C is a perspective end view of another embodiment of a spinal rod in accordance with the present invention.

In another embodiment, shown in FIG. 13C, the pivoting element can be adapted to engage a proximal end of the spinal rod. The engagement between the pivoting element and the proximal end of the spinal rod is preferably an internal engagement, rather than an external engagement, and in an exemplary embodiment, as shown, the spinal rod 170' includes a threaded, blind bore 171' formed therein for receiving a threaded engagement mechanism formed on the pivoting element. In this embodiment, the pivoting element is preferably similar to pivoting element 14 shown in FIGS. 6A and 6B, such that the threaded engagement mechanism, e.g., set screw 60 engages the proximal end of the rod 170'.

Referring back to FIG. 12, in use, due to the configuration of the pivoting member 114 and the position of the set screw 160, the driver shaft can only couple to and rotate the set screw 160 when the pivoting element 114 is moved into the second position. Thus, the trigger 118 must be actuated to move the pusher shaft to move the pivoting element 114 from the first position to the second position. Once in the second position, the driver shaft, which can be an exteriorly placed screw driver, can be positioned through the bore 113 in the proximal portion 112*p* of the elongate shaft 112 to insert the distal end of the driver shaft into the head of the set screw 160. The driver shaft can then be rotated to engage and release the rod 170.

A person skilled in the art will appreciate that a variety of other techniques can be used to mate an implant to the pivoting element of the present invention. By way of non-limiting example, where the implant is a spinal rod, any type of clamping mechanism can be used to releasably engage the rod.

Other mating elements in addition to clamps include, for example, hooks, dimples, and ball plungers.

The present invention also provides methods for percutaneously introducing an implant into a surgical site. The method can be used to introduce any type of implant, and it can be achieved using a variety of inserter tools. The method can also be used with a variety of percutaneous access devices, including, for example, trocars, percutaneous access tubes, etc. An exemplary percutaneous access device for use with the present invention is disclosed in an application entitled "Percutaneous Access Devices and Bone Anchor Assemblies," filed concurrently herewith.

Figure 10C:
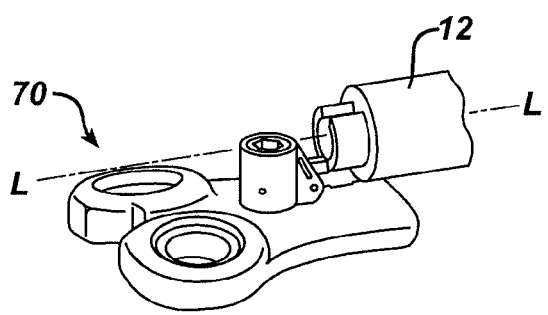
FIG. 10C is a side perspective view of the anterior buttress plate and medical inserter tool shown in FIG. 10B with the plate in an in-line position.

In an exemplary embodiment, the method utilizes a percutaneous access device that is positioned through a minimally invasive incision such that a portion of the access device remains outside of the patient's body, and the remainder of the access device provides a pathway to a surgical site. An exemplary access device and methods for implanting the same is disclosed in an application entitled "Methods and Devices for Minimally Invasive Spinal Fixation Element Placement," filed concurrently herewith and incorporated by reference in its entirety The method includes the steps of introducing an implant holder having an implant mated to a distal end thereof into the percutaneous access device in a lengthwise orientation, with the implant oriented in a direction that is substantially parallel to the longitudinal axis of the implant holder. Thus, for example, where spinal plate 70 is being implanted, the trigger 18 is actuated to hold the pivoting element 14 in the second position, as shown in FIG. 10C. Alternatively, where spinal rod 170 is being implanted, the pivoting element 114 is in the first position, as shown in FIG. 11, with the trigger 118 released.

Figure 14:
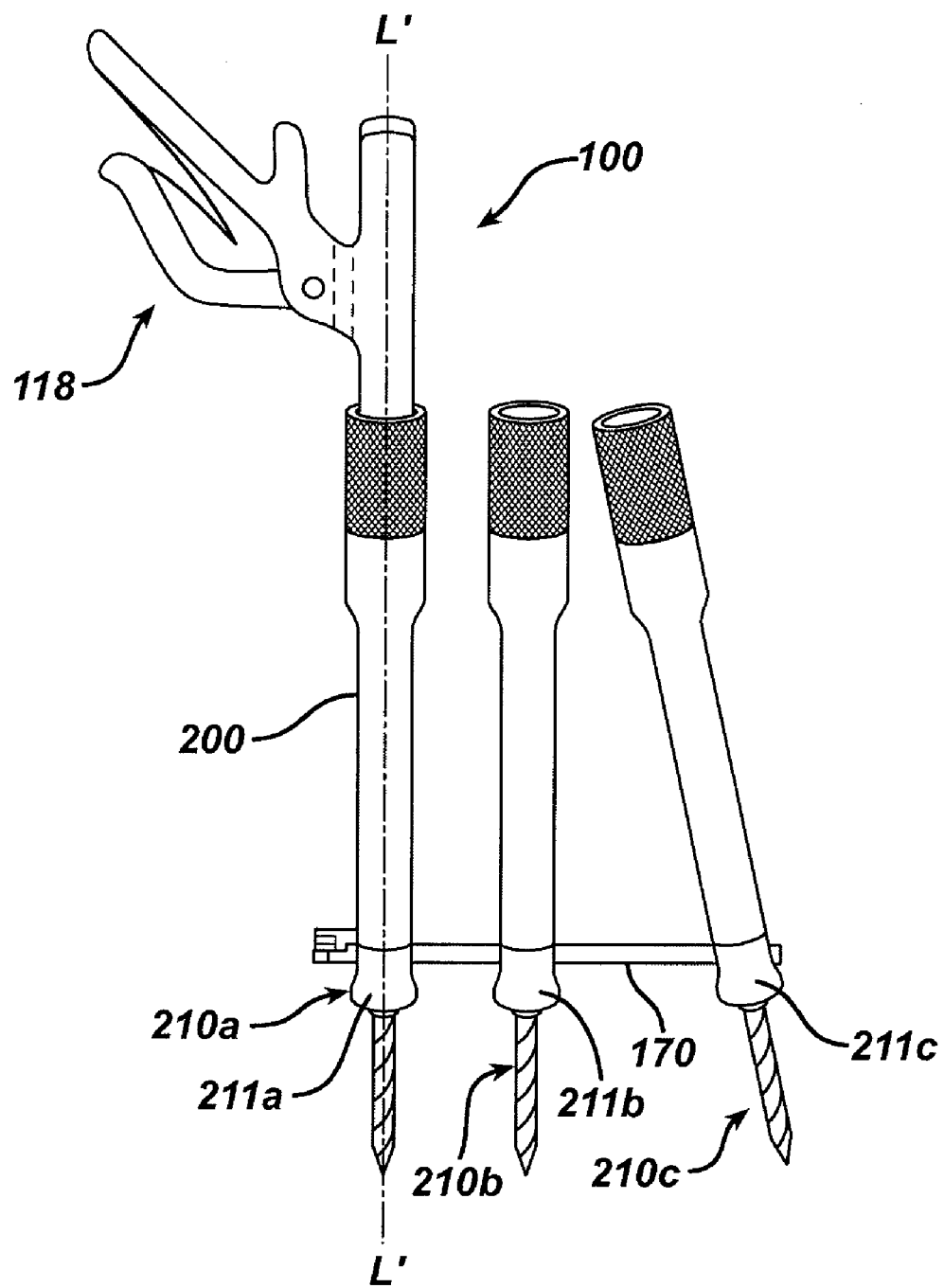
FIG. 14 is side perspective view of the medical inserter tool shown in FIG. 11 disposed through a percutaneous access tube that is coupled to a spinal anchor.

The implant holder 10, 100 is then advanced distally to position the implant 70, 170 at a surgical site. The trigger 18, 118 can then be released or actuated, depending on the configuration of the device 10, 100, to pivot the pivoting element 12, 114 and rotate the implant 70, 170 into a desired position. FIG. 14, for example, illustrates implant holder 100 inserted through a percutaneous access tube 200 that is coupled to spinal anchor 210a. As shown, the trigger 118 is actuated to extend the rod 170 in a direction that is substantially transverse to the longitudinal axis E of the implant holder 100, thereby positioning the rod 170 in the rod-receiving head 211a-c of several adjacent spinal anchors 210a-c. The implant holder 10, 100 can then be released from the implant 70, 170, for example, by rotating the driver shaft to unthread the set screw 60, 160 from the implant 70, 170, and the implant holder 10, 100 can be removed from the percutaneous access tube.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for introducing a spinal rod into a surgical site, comprising: advancing a spinal rod having a proximal end coupled to a distal end of a pivoting element on a distal end of an inserter tool through a percutaneous access device; actuating a trigger mechanism on the inserter tool to move the pivoting element about a pivot point at a proximal end of the pivoting element from a first position in which the pivoting element extends coaxial with a longitudinal axis of the inserter tool and the spinal rod extends substantially parallel to the longitudinal axis of the inserter tool, to a second position in which the pivoting element extends transverse to the longitudinal axis of the inserter tool.

2. The method of claim 1, further comprising rotating a driver shaft relative to the pivoting element to release the proximal end of the spinal rod from engagement with the pivoting element.

3. The method of claim 2, further comprising, prior to rotating the driver shaft, positioning the driver shaft to extend parallel to the longitudinal axis of the inserter tool.

4. The method of claim 2, wherein the spinal rod is engaged by a threaded member freely rotatably disposed within the pivoting element, and wherein rotating the driver shaft relative to the pivoting element rotates the threaded member to release the spinal rod from the pivoting element.

5. The method of claim 1, wherein the percutaneous access device has a distal end mated to a spinal anchor, and wherein advancing a spinal rod through the percutaneous access device is effective to deliver the spinal rod to the spinal anchor.

6. The method of claim 1, wherein the spinal rod is advanced in an orientation parallel to the longitudinal axis of the inserter tool.

7. A method for introducing a spinal rod into a surgical site, comprising: advancing a spinal rod coupled to an inserter tool through an access device defining a pathway extending through tissue to a surgical site; actuating a trigger mechanism on the inserter tool to transition the spinal rod from a first orientation in which the spinal rod extends substantially parallel to a longitudinal axis of inserter tool, to a second orientation in which the spinal rod extends transverse to the longitudinal axis of the inserter tool; and rotating a driver shaft about a longitudinal axis of the driver shaft relative to the inserter tool to release the spinal rod from the inserter tool, the driver shaft being positioned offset from the longitudinal axis of the inserter tool.

8. The method of claim 7, wherein the access device is mated to a spinal anchor implanted in a vertebra.

9. The method of claim 7, further comprising, prior to rotating the driver shaft, positioning the driver shaft to extend parallel to the longitudinal axis of the inserter tool.

10. The method of claim 7, wherein rotating the driver shaft relative to the inserter tool rotates a threaded engagement mechanism on the inserter tool to threadably release the spinal rod from engagement with the threaded engagement mechanism.

11. The method of claim 7, wherein the spinal rod is coupled to a pivoting element pivotally coupled to a distal end of the inserter tool, and actuating the trigger mechanism on the inserter tool pivots a pivoting element to transition the spinal rod from the first orientation to the second orientation.

12. The method of claim 11, wherein the pivoting element extends coaxial with the longitudinal axis of the inserter tool when the spinal rod is in the first orientation, and the pivoting element extends transverse to the longitudinal axis of the inserter tool when the spinal rod is in the second orientation.

13. A method for percutaneously introducing a spinal rod into a surgical site, comprising: introducing an elongate rod holder having a distal end mated to a proximal terminal end of a spinal rod into a percutaneous access device that is coupled to a spinal anchor disposed in bone, the percutaneous access device providing a minimally invasive pathway to the spinal anchor, and the spinal rod being oriented in a first position substantially parallel to a longitudinal axis of the elongate rod holder when the elongate rod holder is in the percutaneous access device; advancing the elongate rod holder through the percutaneous access device to position the spinal rod relative to the spinal anchor; causing the elongate rod holder to move the spinal rod into a second position in which the spinal rod is oriented substantially transverse to the longitudinal axis of the elongate rod holder and the proximal terminal end of the rod is positioned in the spinal anchor; and rotating a driver shaft relative to the inserter tool to release the spinal rod from the inserter tool.

14. The method of claim 13, further comprising removing the elongate rod holder from the percutaneous access device.

15. The method of claim 13, wherein the driver shaft is positioned offset from a longitudinal axis of the elongate rod holder.

16. The method of claim 13, wherein rotating the driver shaft rotates a threaded member threadably disposed within a threaded bore formed in the spinal rod to release the spinal rod from the threaded member.

17. The method of claim 13, wherein causing the elongate rod holder to move the spinal rod into the second position comprises actuating a trigger mechanism coupled to the elongate rod holder to pivot a pivoting element pivotally coupled to the distal end of the elongate rod holder, the pivoting element being releasably engaged with the spinal rod.

18. The method of claim 17, wherein the pivoting element is coaxial with a longitudinal axis of the elongate rod holder when the spinal rod is in the first position, and wherein the pivoting element extends transverse to the longitudinal axis of the elongate rod holder when the spinal rod is in the second position.

19. The method of claim 17, wherein the pivoting element is biased to the first position, and the trigger mechanism is actuated after introduction and advancement of the elongate rod holder through the percutaneous access device.

20. The method of claim 13, wherein a distal end of the spinal rod holder engages a proximal, trailing end of the spinal rod, and a distal, leading end of the spinal rod is advanced into the percutaneous access device.

* * * * *